(12) United States Patent
Arimura et al.

(10) Patent No.: US 10,357,412 B2
(45) Date of Patent: Jul. 23, 2019

(54) STRETCHER

(71) Applicants: FUJIDENOLO CO., LTD., Komaki-shi, Aichi (JP); MEDIPOLIS MEDICAL RESEARCH INSTITUTE, Ibusuki-shi, Kagoshima (JP)

(72) Inventors: Takeshi Arimura, Ibusuki (JP); Mitsugi Matsuyama, Ibusuki (JP); Yoshio Hishikawa, Ibusuki (JP); Takashi Ogino, Ibusuki (JP); Hideki Miyazaki, Komaki (JP); Keiichi Noma, Komaki (JP); Akari Sakuragi, Komaki (JP)

(73) Assignees: FUJIDENOLO CO., LTD., Komaki (JP); MEDIPOLIS MEDICAL RESEARCH INSTITUTE, Kagoshima (JP)

( * ) Notice: Subject to any disclaimer, the term of this patent is extended or adjusted under 35 U.S.C. 154(b) by 0 days.

(21) Appl. No.: 15/317,728

(22) PCT Filed: Jun. 15, 2015

(86) PCT No.: PCT/JP2015/067219
§ 371 (c)(1),
(2) Date: Dec. 9, 2016

(87) PCT Pub. No.: WO2015/194515
PCT Pub. Date: Dec. 23, 2015

(65) Prior Publication Data
US 2017/0112692 A1   Apr. 27, 2017

(30) Foreign Application Priority Data
Jun. 16, 2014 (JP) ................. 2014-123848

(51) Int. Cl.
*A61G 1/02*      (2006.01)
*A61G 1/003*     (2006.01)
*F17C 1/00*      (2006.01)

(52) U.S. Cl.
CPC .......... *A61G 1/0293* (2013.01); *A61G 1/003* (2013.01); *A61G 1/02* (2013.01); *A61G 1/0212* (2013.01);
(Continued)

(58) Field of Classification Search
CPC .... A61G 1/0293; A61G 1/0287; A61G 1/003; A61G 1/0212; A61G 1/02; F17C 1/00; F17C 2205/0394
(Continued)

(56) References Cited

U.S. PATENT DOCUMENTS 5,015,024 A * 5/1991 Bloemer .............. A61G 1/0293
280/767
5,022,105 A * 6/1991 Catoe ................... A61G 1/0567
296/20
(Continued)

FOREIGN PATENT DOCUMENTS

CN      2628019 Y     7/2004
CN    201076569 Y     6/2008
(Continued)

OTHER PUBLICATIONS

Dec. 20, 2016 International Preliminary Report on Patentability issued in International Patent Application No. PCT/JP2015/067219.
(Continued)

*Primary Examiner* — Pamela Rodriguez
(74) *Attorney, Agent, or Firm* — Oliff PLC

(57)  ABSTRACT

A stretcher has a rectangle-shaped subject placement portion on which a subject is placed and a carrying device carrying the subject placement portion, comprising: a switching part
(Continued)

switched to any one of at least two states; and a switching device switching a state of the switching part in accordance with a supplied gas pressure. The at least two states include a state in which the switching part prevents movement of the subject placement portion and a state in which the switching part allows the movement.

5 Claims, 9 Drawing Sheets

(52) U.S. Cl.
CPC ............. *A61G 1/0287* (2013.01); *F17C 1/00* (2013.01); *F17C 2205/0394* (2013.01)

(58) Field of Classification Search
USPC ..... 188/23, 1.12, 5, 19; 5/81.1 R, 86.1, 600, 5/611, 616; 296/20
See application file for complete search history.

(56) References Cited

U.S. PATENT DOCUMENTS

| | | | | |
|---|---|---|---|---|
| 5,365,622 | A * | 11/1994 | Schirmer | A61G 1/0565 5/611 |
| 5,537,700 | A | 7/1996 | Way et al. | |
| 6,976,696 | B2 * | 12/2005 | O'Krangley | A61G 1/0562 280/638 |
| 7,409,734 | B2 * | 8/2008 | Benedict | A61G 1/0567 296/20 |
| 8,452,508 | B2 * | 5/2013 | Frolik | A61G 7/018 180/19.1 |
| 2006/0225203 | A1 | 10/2006 | Hosoya et al. | |
| 2007/0079439 | A1 * | 4/2007 | Patterson | A61G 7/1019 5/81.1 R |

FOREIGN PATENT DOCUMENTS

| | | |
|---|---|---|
| CN | 101336859 A | 1/2009 |
| CN | 201422979 Y | 3/2010 |
| CN | 202069782 U | 12/2011 |
| CN | 202161495 U | 3/2012 |
| JP | H05-56123 U | 7/1993 |
| JP | 2000-233245 A | 8/2000 |
| JP | 2005-021628 A | 1/2005 |
| JP | 2006-218022 A | 8/2006 |
| JP | 2012-105746 A | 6/2012 |

OTHER PUBLICATIONS

Sep. 1, 2015 International Search Report issued in International Patent Application No. PCT/JP2015/067219.
Sep. 1, 2017 Office Action issued in Chinese Patent Application No. 201580032021.4.
Nov. 21, 2017 Search Report issued in European Patent Application No. 15810460.4.
Aug. 21, 2018 Office Action issued in Japanese Patent Application No. 2014-123848.

* cited by examiner

FIG.6
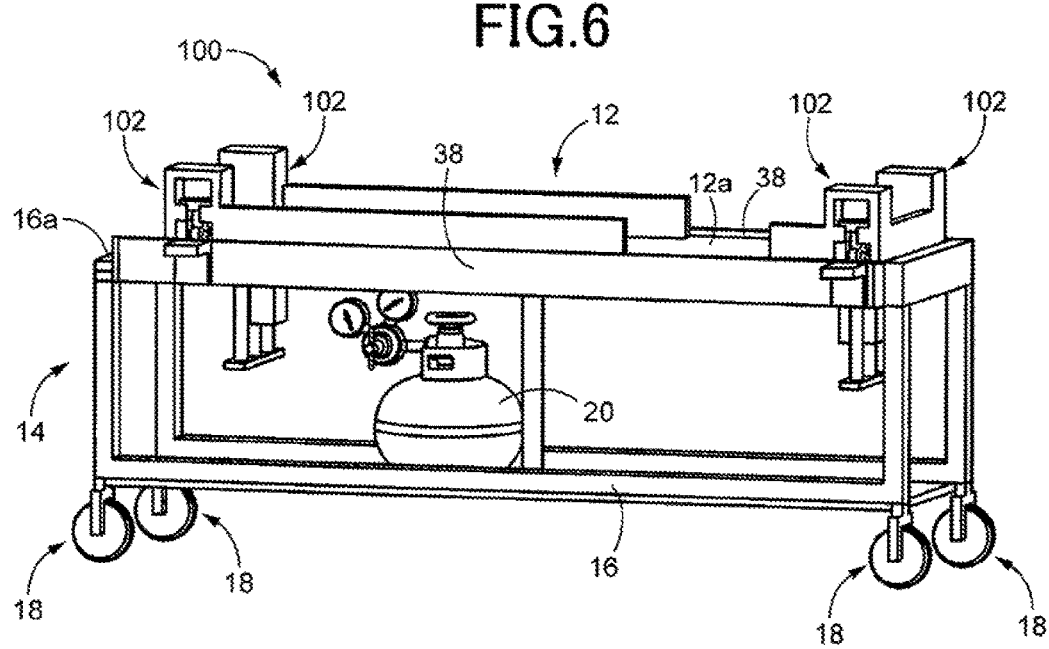
FIG.7
(a) 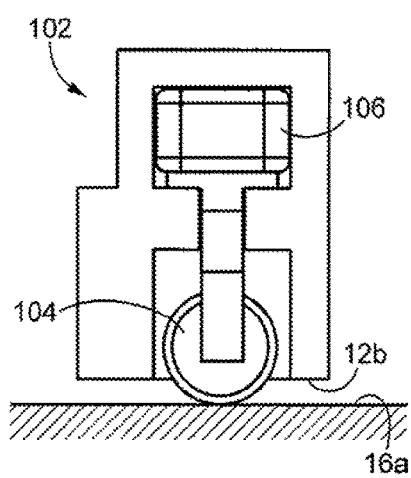
(b) 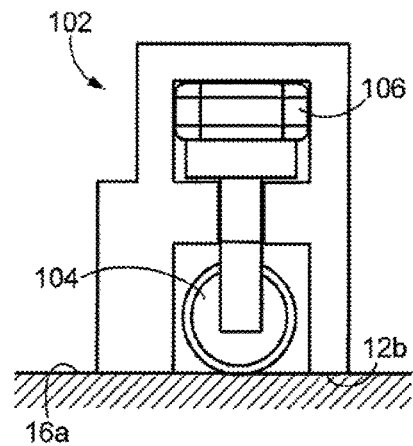

FIG.8
(a) 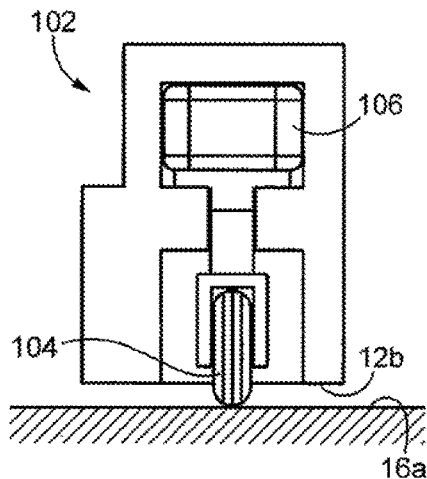
(b) 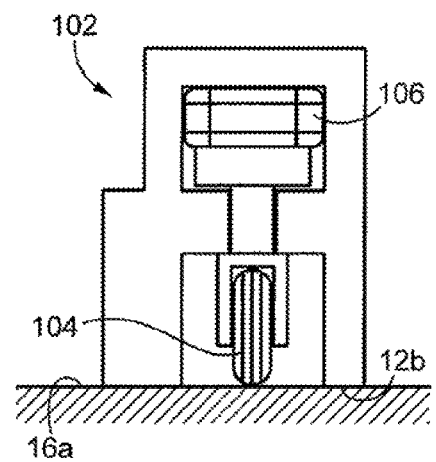
FIG.9
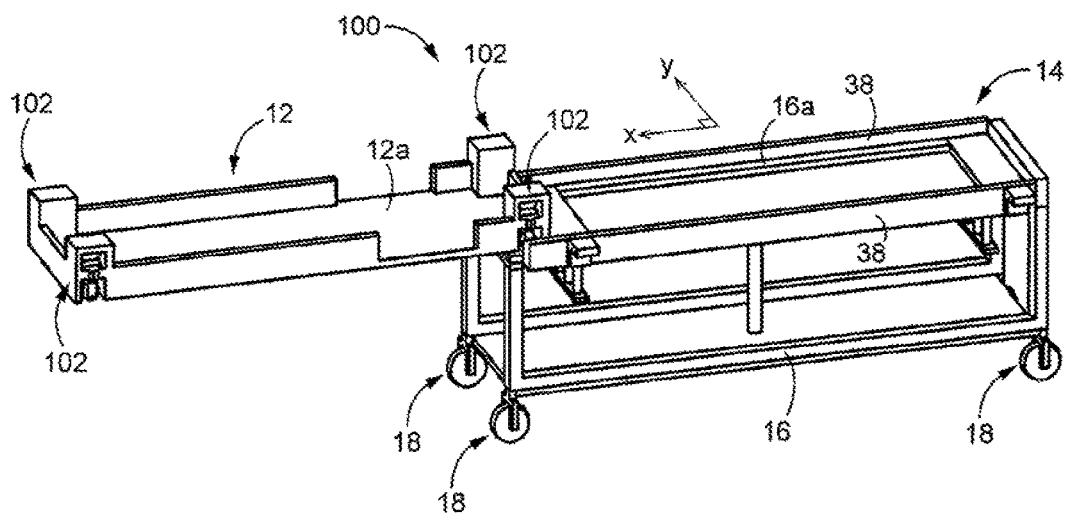

ively simple structure, sufficient durability can be ensured
STRETCHER

TECHNICAL FIELD

The present invention relates to a stretcher for carrying a subject at the time of examination using a nuclear magnetic resonance apparatus etc.

BACKGROUND ART

A stretcher is known that includes a subject placement portion on which a subject is placed and a carrying device carrying the subject placement portion. In such a stretcher, after the subject placement portion with a subject placed thereon is carried by the carrying device, the subject placement portion is moved from the carrying device to another place. Techniques have been proposed for making such a movement easier. For example, a slide mechanism of a placement table of a stretcher described in Patent Document 1 is an example thereof. According to this technique, after the placement table is moved by a carrying device to near a bed, the placement table can easily be moved by the slide mechanism to a center portion of the bed.

PRIOR ART DOCUMENT

Patent Document

Patent Document 1: Japanese Laid-Open Patent Publication No. 2012-105746

SUMMARY OF THE INVENTION

Problem to be Solved by the Invention

However, considering a long side direction and a short side direction of a rectangular subject placement portion, the conventional technique has a problem that the subject placement portion can only be moved in one of the directions relative to the carrying device. Additionally, although a stretcher for carrying a subject at the time of examination using a nuclear magnetic resonance apparatus (Magnetic Resonance Imager; MRI) should comply with a specification in which a magnetic material is not used, it is difficult for the conventional technique to achieve easy movement of the subject placement portion from the carrying device while satisfying such a specification. Such a problem was newly found out by the present inventors in the course of continuing extensive studies with the intention of developing a convenient easy-to-use stretcher.

The present invention was conceived in view of the situations and it is therefore an object of the present invention to provide a stretcher achieving easy movement of a subject placement portion from a carrying device.

Solution to Problem

To achieve the above object, a first aspect of the present invention provides a stretcher having a rectangle-shaped subject placement portion on which a subject is placed and a carrying device carrying the subject placement portion, comprising: a switching part switched to any one of at least two states; and a switching device switching a state of the switching part in accordance with a supplied gas pressure.

Advantageous Elects of Invention

According to the first aspect of the invention, since the stretcher includes the switching part switched to any one of at least the two states of the switching part and the switching device switching the state of the switching part in accordance with a supplied gas pressure, the state of the predetermined switching part in the stretcher can appropriately be switched by a power source complying with a specification in which a magnetic material is not used. This enables the provision of the stretcher achieving easy movement of the subject placement portion from the carrying device.

A second aspect of the present invention provides the stretcher recited in the first aspect of the invention, comprising, a gas cylinder mounted on the carrying device and filled with a compressed gas, wherein the gas cylinder is made of a non-magnetic material and supplies a gas pressure to the switching device. Consequently, the switching by the switching device can be achieved in a safe and practical form.

A third aspect of the present invention provides the stretcher recited in the first or second aspect of the invention, wherein the subject placement portion includes as the switching part a set of wheels rotating in a long side direction of the subject placement portion, and a set of wheels rotating in a short side direction of the subject placement portion, and wherein the switching device switches between a first state in which the wheels are at least partially protruded from a flat surface portion on the side opposite to a flat surface portion on the side of the subject placement portion on which the subject is placed and a second state in which the wheels are not protruded, correspondingly to each of the set of wheels rotating in the long side direction and the set of wheels rotating in the short side direction. Consequently, the subject placement portion can easily be moved relative to the carrying device in both the long side direction and the short side direction of the subject placement portion and, additionally, because of a comparatively simple structure, sufficient durability can be ensured even if a synthetic resin material is used for the wheels, for example.

A fourth aspect of the present invention provides the stretcher recited in the first or second aspect of the invention, wherein the carrying device includes as the switching part a brake device generating a braking force by abutting an abutting portion on a floor surface on which the carrying device is located, and wherein the switching device switches in accordance with the supplied gas pressure between a first state in which the abutting portion is abutted on the floor surface and a second state in which the abutting portion is separated from the floor surface in the brake device. Consequently, the braking of the carrying device against the floor surface can be achieved by a power source complying with a specification in which a magnetic material is not used.

A fifth aspect of the present invention provides the stretcher recited in the third or fourth aspect of the invention, wherein the stretcher includes a pneumatic circuit using a gas pressure to control switching between the first state and the second state by the switching device. Consequently, the switching by the switching device can be achieved in a safe and practical form.

A sixth aspect of the present invention provides the stretcher recited in any one of the first to fifth aspects of the invention, wherein the subject placement portion and the carrying device have major portions made of a non-magnetic material. Consequently, the stretcher can be provided that is preferably used at the time of examination using a nuclear magnetic resonance apparatus.

Alternatively, the pneumatic circuit may use a gas pressure supplied from outside piping etc. to control the switching between the first state and the second state by the switching device. The stretcher may include a vacuum pump and a pneumatic circuit using a suction air of the vacuum pump to control the switching between the first state and the second state by the switching device.

BRIEF DESCRIPTION OF DRAWINGS

FIG. 6 is a perspective view for explaining an example of a configuration of a stretcher that is another preferred embodiment of the present invention.

FIGS. 7A and 7B are schematic side views for explaining a configuration of a wheel unit included in the subject placement portion of the stretcher of FIG. 6, exemplarily illustrating a form including a wheel rotating in the long side direction of the subject placement portion.

FIGS. 8A and 8B are schematic side views for explaining a configuration of the wheel unit included in the subject placement portion of the stretcher of FIG. 6, exemplarily illustrating a form including a wheel rotating in the short side direction of the subject placement portion.

FIG. 9 is a perspective view for explaining how the subject placement portion is moved in the long side direction relative to the carrying device in the stretcher of FIG. 6.

MODES FOR CARRYING OUT THE INVENTION

Figure 1:
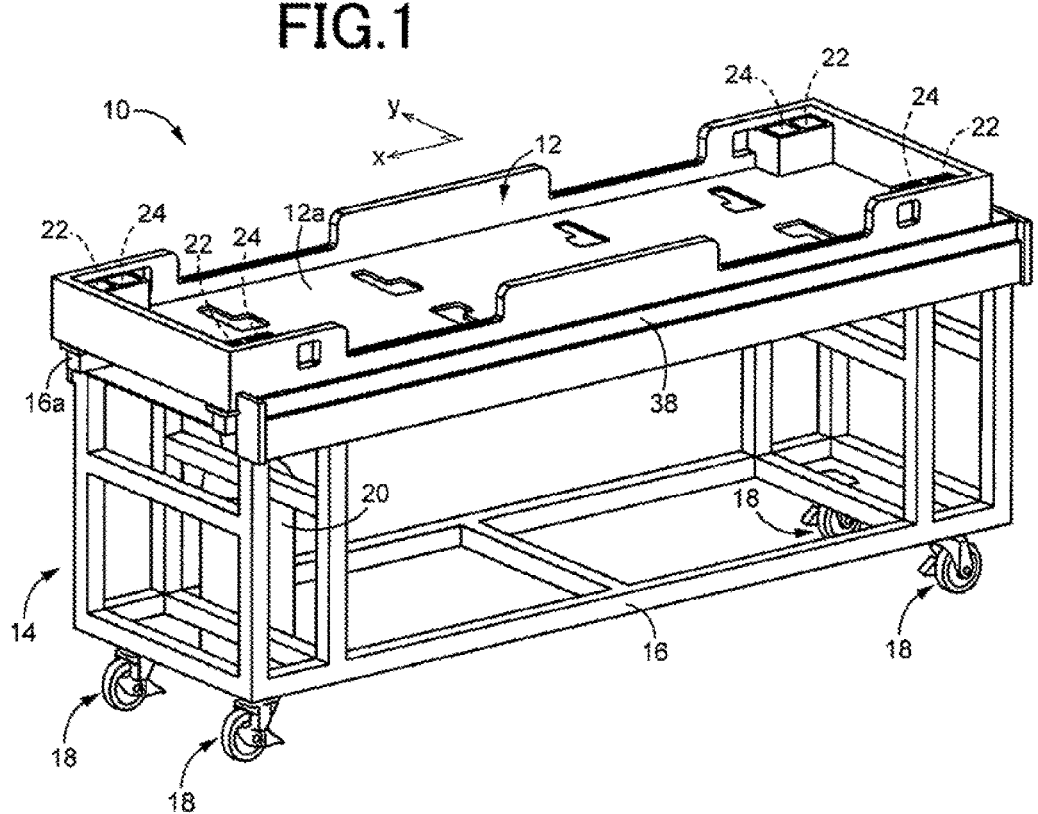
FIG. 1 is a perspective view for explaining an example of a configuration of a stretcher that is a preferred embodiment of the present invention.

A preferred embodiment of the present invention will now be described in detail with reference to the drawings. In the drawings used in the following description, the portions are not necessarily precisely drawn in terms of dimension ratio etc.

First Embodiment

FIG. 1 is a perspective view for explaining a configuration of a stretcher 10 that is a preferred embodiment of the present invention. This stretcher 10 includes, for example, a subject placement portion 12 on which a subject not shown is placed and a carrying device 14 carrying the subject placement portion 12. The carrying device 14 includes a frame 16 made of a non-magnetic material such as an aluminum alloy, for example, and a plurality of in FIG. 1, four) casters 18 attached on a lower portion of the frame 16. In this embodiment, the non-magnetic material may be a metal material having a negligible effect on a magnetic field, such as an aluminum alloy, a titanium alloy, and a copper alloy, a synthetic resin material, or a wood material.

The casters 18 are known caster devices each including a wheel having a wheel diameter of 100 mmϕ or more, for example, and allowing an axle of the wheel to freely rotate 360° in a plane parallel to a floor surface (a floor surface on which the carrying device 14 is disposed), and have all the components made of a non-magnetic material. The casters 18 each include a known lock mechanism switching between states of preventing and permitting the rotation of the wheel. These lock mechanisms preferably switch between the states of preventing and permitting the rotation of the respective wheels of the plurality of the casters 18 at the same time (e.g., in accordance with one operation). The lock mechanisms may use a gas pressure supplied from a gas cylinder 20 described later for the switching described above.

The stretcher 10 includes the known gas cylinder 20 filled with a compressed gas. This gas cylinder 20 is an inert gas cylinder made of a non-magnetic material such as an aluminum alloy, for example, and filled with an inert gas including a carbonic acid gas (carbon dioxide); however, the gas cylinder may be filled with an air etc. The gas cylinder 20 is preferably mounted on the carrying device 14. Specifically, the gas cylinder 20 is fixed to the frame 16 and is moved in accordance with the movement of the frame 16.

The subject placement portion 12 is a flat plate-shaped member having a rectangular shape in a planar view and is made of a non-magnetic material such as a synthetic resin material, for example. For example, the rectangle-shaped member has a peripheral edge portion provided with an edge portion protruding toward an upper surface 12a side on which the subject is placed. Therefore, in other words, the subject placement portion 12 is a box-shaped member without an upper surface having a rectangular shape in a planar view. The subject placement portion 12 preferably has all the components including wheel units 22, 24 etc. described later made of a synthetic resin material.

When carried by the carrying device 14, the subject placement portion 12 is mounted on a mounting table 16a disposed on an upper portion (the vertically upper side) of the frame 16 as shown in FIG. 1. This mounting table 16a is disposed at a height of about 750 mm from the floor surface on which the carrying device 14 is disposed, for example. Preferably, a pair of side plates 38 for preventing the subject placement portion 12 placed on the mounting table 16a from falling is attached to both side portions in the long side direction of the mounting table 16a. When a subject is carried with the stretcher 10, the subject not shown is placed on the upper surface 12a that is one flat surface portion of the subject placement portion 12 mounted on the mounting table 16a. Preferably, the subject is fixed by a subject fixture not shown to the subject placement portion 12. Therefore, in other words, the subject placement portion 12 is a subject fixing portion with the subject fixed to the one flat surface portion when carried by the carrying device 14.

Figure 2:
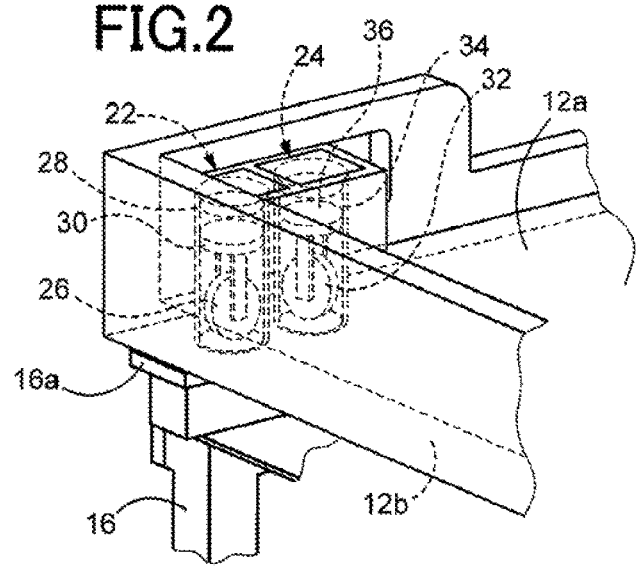
FIG. 2 is a view for explaining wheel units of the subject placement portion included in the stretcher of FIG. 1, partially showing with imaginary lines.

The subject placement portion 12 includes a set of the wheel units 22 for actuation related to a set of wheels 26 rotating in the long side direction of the subject placement portion 12, and a set of the wheel units 24 for actuation related to a set of wheels 32 rotating in the short side direction of the subject placement portion 12. FIG. 2 is a partially cutaway view for explaining the wheel units 22, 24 included in the subject placement portion 12, showing the wheel units 22, 24 built into the subject placement portion 12 with imaginary lines (broken lines). As shown in FIG. 1, for example, one each of the wheel units 22, 24 is disposed at each of the four corners of the subject placement portion 12. Therefore, the subject placement portion 12 includes multiple pain (in FIG. 1, two pairs) constituting each of the sets of the wheel units 22, 24, and FIG. 2 exemplarily illustrates a configuration of one each of the wheel units 22, 24.

The plurality of the wheel units 22 is disposed correspondingly to movement (transfer) in the long side direction of the subject placement portion 12 relative to the carrying device 14. The long side direction of the subject placement portion 12 is the direction of the long sides when the subject placement portion 12 is viewed as a rectangle in a planar view, and corresponds to an X-axis direction shown in FIG. 1. As shown in FIG. 2, the wheel units 22 each include, the wheel 26 with a direction of an axle determined to rotate in the long side direction of the subject placement portion 12 and a cylinder (cylinder driven by air) 28, and the wheel 26 is attached to a piston 30 included in the cylinder 28. The cylinder 28 is built into the subject placement portion 12 such that an end portion (a bottom surface of a circular column) on the side provided with the wheel 26 is opened in a bottom surface 12b of the subject placement portion 12. This bottom surface 12b corresponds to a flat surface portion on the side opposite to the upper surface 12a defined as the flat surface portion on the side of the subject placement portion 12 on which the subject is placed. The bottom surface 12b is the flat surface portion brought into contact with the mounting table 16a when both the wheels 26, 32 are put into a second state described later.

The plurality of the wheel units 24 is disposed correspondingly to movement (transfer) in the short side direction of the subject placement portion 12 relative to the carrying device 14. The short side direction of the subject placement portion 12 is the direction of the short sides when the subject placement portion 12 is viewed as a rectangle in a planar view, and corresponds to a y-axis direction shown in FIG. 1. As shown in FIG. 2, the wheel units 24 each include the wheel 32 with a direction of an axle determined to rotate in the short side direction of the subject placement portion 12 and a cylinder (cylinder driven by air) 34, and the wheel 32 is attached to a piston 36 included in the cylinder 34. The cylinder 34 is built into the subject placement portion 12 such that an end portion (a bottom surface of a circular column) on the side provided with the wheel 32 is opened in a bottom surface 12b of the subject placement portion 12.

The cylinders 28, 34 are switched between a first state in which the wheels 26, 32 are at least partially protruded from the bottom surface 12b and a second state in which the wheels are not protruded, in accordance with a gas pressure supplied from a pneumatic circuit 40 described later. Specifically, the pistons 30, 36 are pushed out in the direction of protruding the wheels 26, 32 from the bottom surface 12b by the gas pressure supplied from the pneumatic circuit 40. When a gas pressure of a predetermined value or more is supplied to the cylinders 28, 34 while the wheels 26, 32 are in contact with the mounting table 16a of the frame, the wheels 26, 32 are at least partially protruded from the bottom surface 12b such that the subject placement portion 12 is separated from the mounting table 16a (i.e., the subject placement table 12 is lifted) against the weight (gravity force) of the subject placement portion 12 and the subject etc. placed on the subject placement portion 12. Therefore, in this embodiment, the wheels 26, 32 correspond to a switching part switched to any one of at least two states. The cylinders 28, 34 correspond to a switching device switching between the first state in which the wheels 26, 32 are at least partially protruded from the bottom surface 12b of the subject placement portion 12 and the second state in which the wheels are not protruded (i.e., stored in the subject placement portion 12), correspondingly to each of the set of the wheels 26 rotating in the long side direction and the set of the wheels 32 rotating in the short side direction.

Figure 3:
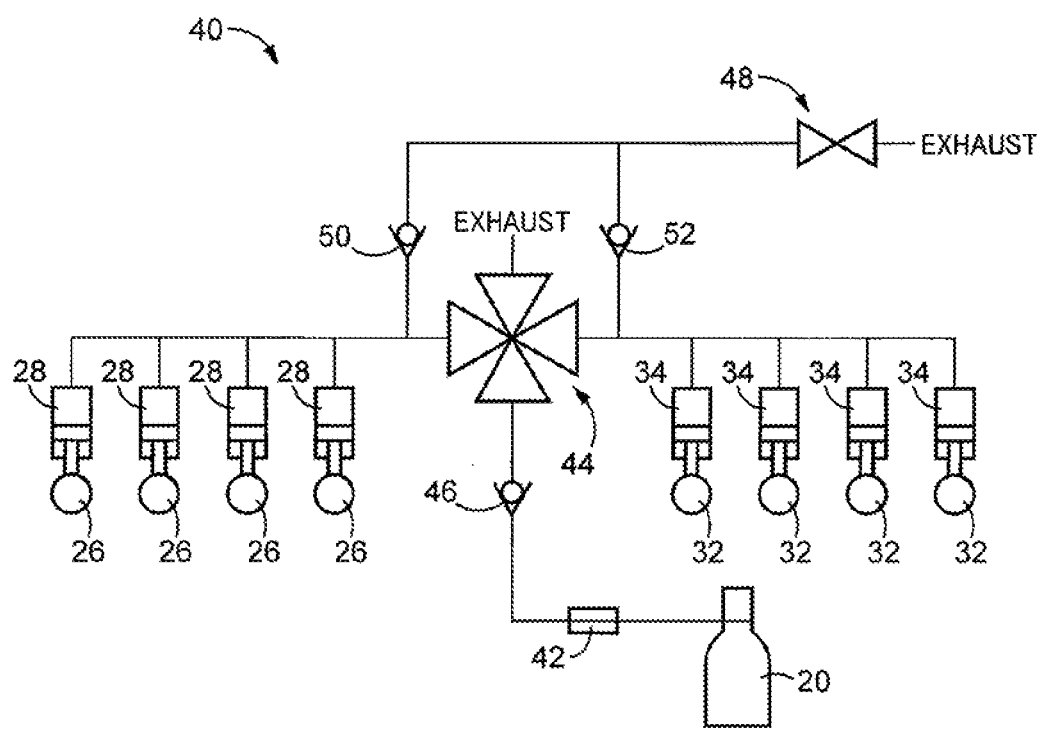
FIG. 3 is a circuit diagram for explaining a main portion of an example of the pneumatic circuit included in the stretcher of FIG. 1.

FIG. 3 is a circuit diagram for explaining a main portion of an example of the pneumatic circuit 40 included in the stretcher 10 to control the switching between the first state and the second state by the cylinders 28, 34. This pneumatic circuit 40 (including a coupling portion 42) is preferably made of a non-magnetic material. The pneumatic circuit 40 is preferably included in the subject placement portion 12. The gas cylinder 20 is made attachable to and detachable from the pneumatic circuit 40 by the coupling portion 42 such as a known joint. A first valve 44 is disposed between the coupling portion 42 and the plurality of the cylinders 28, 34. Between the first valve 44 and the coupling portion 42, a check valve 46 is disposed that permits a gas to flow in from the coupling portion 42 toward the first valve 44 while preventing a backward flow of the gas from the first valve 44 toward the coupling portion 42. In particular, the check valve 46 is included on the subject placement portion 12 side relative to the coupling portion 42 to prevent the backward flow of the gas from the pneumatic circuit 40 toward the coupling portion 42. A second valve 48 is disposed between the plurality of the cylinders 28, 34 and an exhaust port. Between the second valve 48 and the plurality of the cylinders 28, a check valve 50 is disposed that permits a gas to flow in from the plurality of the cylinders 28 toward the second valve 48 while preventing a backward flow of the gas from the second valve 48 toward the plurality of the cylinders 28. Between the second valve 48 and the plurality of the cylinders 34, a check valve 52 is disposed that permits a gas to flow in from the plurality of the cylinders 34 toward the second valve 48 while preventing a backward flow of the gas from the second valve 48 toward the plurality of the cylinders 34.

The first valve 44 has, for example, a state of a valve piece switched to selectively establish the following four circuits. Specifically, in a first state of the valve, the valve establishes the circuit, allowing communication between the coupling portion 42 and the plurality of the cylinders 28 to supply the gas pressure of the gas cylinder 20 to the plurality of the cylinders 28. In this circuit, communication is interrupted between the coupling portion 42 and the plurality of the cylinders 34. In a second state of the valve, the valve establishes the circuit allowing communication between the coupling portion 42 and the plurality of the cylinders 34 to supply the gas pressure of the gas cylinder 20 to the plurality of the cylinders 34. In this circuit, communication is interrupted between the coupling portion 42 and the plurality of the cylinders 28. In a third state of the valve, the valve establishes the circuit allowing communication between the coupling portion 42 and the exhaust port. In this circuit, communication is interrupted between the coupling portion 42 and the plurality of the cylinders 28, 34. In a fourth state of the valve, the valve interrupts the inflow of the gas from the coupling portion 42. In other words, the first valve 44 switches the circuit such that the gas pressure of the gas cylinder 20 is selectively supplied to either the plurality of the cylinders 28 or the plurality of the cylinders 34. The second valve 48 is a gate valve having, for example, a state of a valve piece switched to switch between a circuit interrupting the inflow of the gas from the plurality of the cylinders 28, 34 and a circuit allowing communication between the plurality of the cylinders 28, 34 and the exhaust port.

Figure 4:
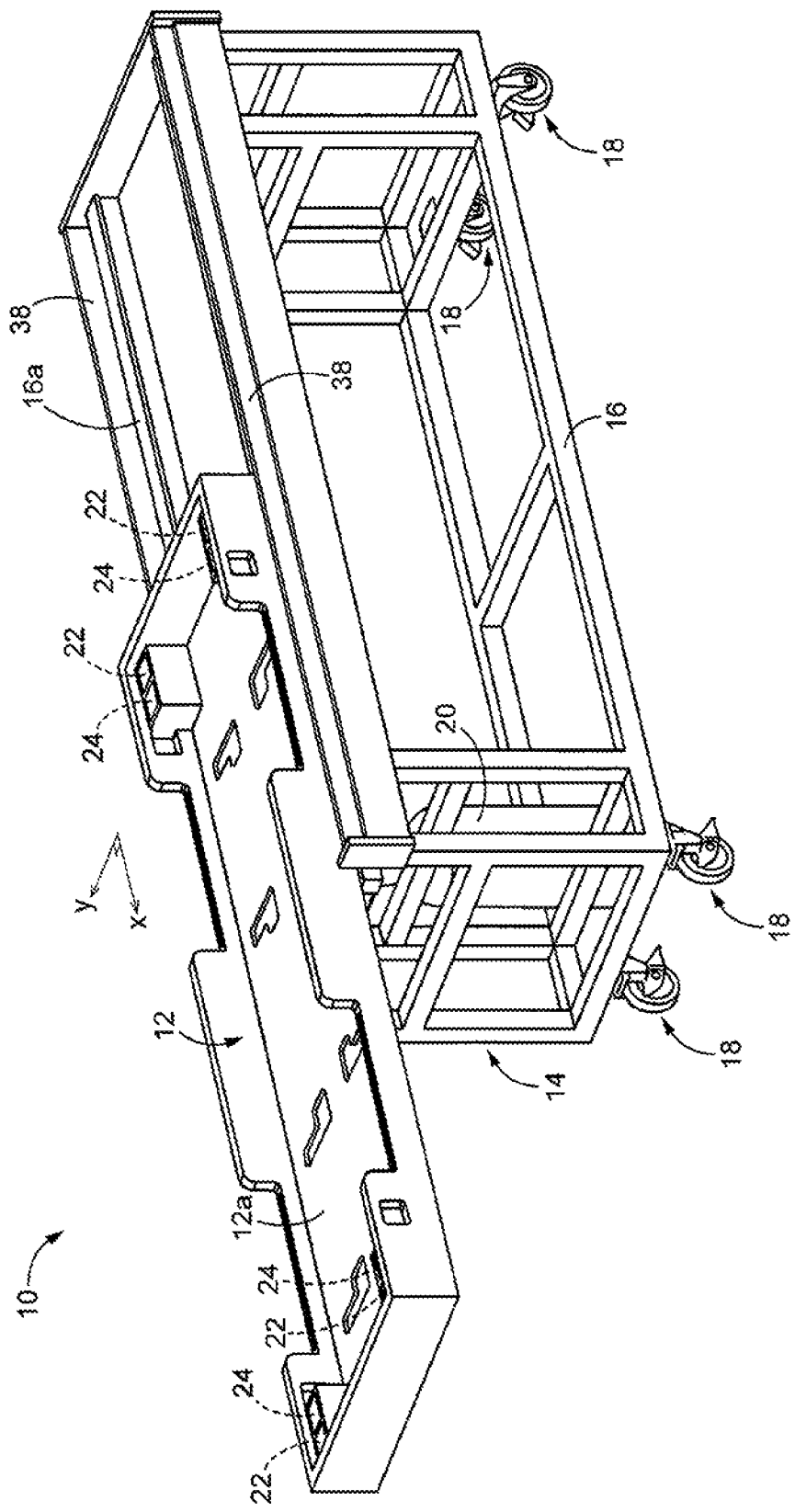
FIG. 4 is a perspective view of how the subject placement portion is moved in the long side direction relative to a carrying device in the stretcher of FIG. 1.

In the pneumatic circuit 40, when the first valve 44 is put into the first state of the valve to allow communication between the coupling portion 42 and the plurality of the cylinders 28, the gas pressure of the gas cylinder 20 is supplied to the plurality of the cylinders 28. In this state, the pistons 30 are pushed out relative to the cylinders 28 by the gas pressure supplied from the gas cylinder 20, and the wheels 26 are at least partially protruded from the bottom surface 12b in the set of the wheel units 22. On the other hand, if the first valve 44 is put into the first state of the valve, the gas pressure of the gas cylinder 20 is not supplied to the plurality of the cylinders 34. Therefore, the wheels 32 are not protruded from the bottom surface 12b in the set attic wheel units 24 and are kept in the state of being stored in the subject placement portion 12. In particular, a set of the wheels 26 in the set of the wheel units 22 disposed correspondingly to the movement in the long side direction of the subject placement portion 12 is brought into contact with the mounting table 16a, and the subject placement portion 12 is put into a state of being separated (lined) from the mounting table 16a by the plurality of the cylinders 28. In this state, because of the rotation of each wheel included in the set of the wheels 26 in the set of the wheel units 22, as shown in FIG. 4, the subject placement portion 12 is easily moved (transferred) in the long side direction (the x-axis direction shown in FIG. 4) relative to the carrying device 14 (the mounting table 16a).

Figure 5:
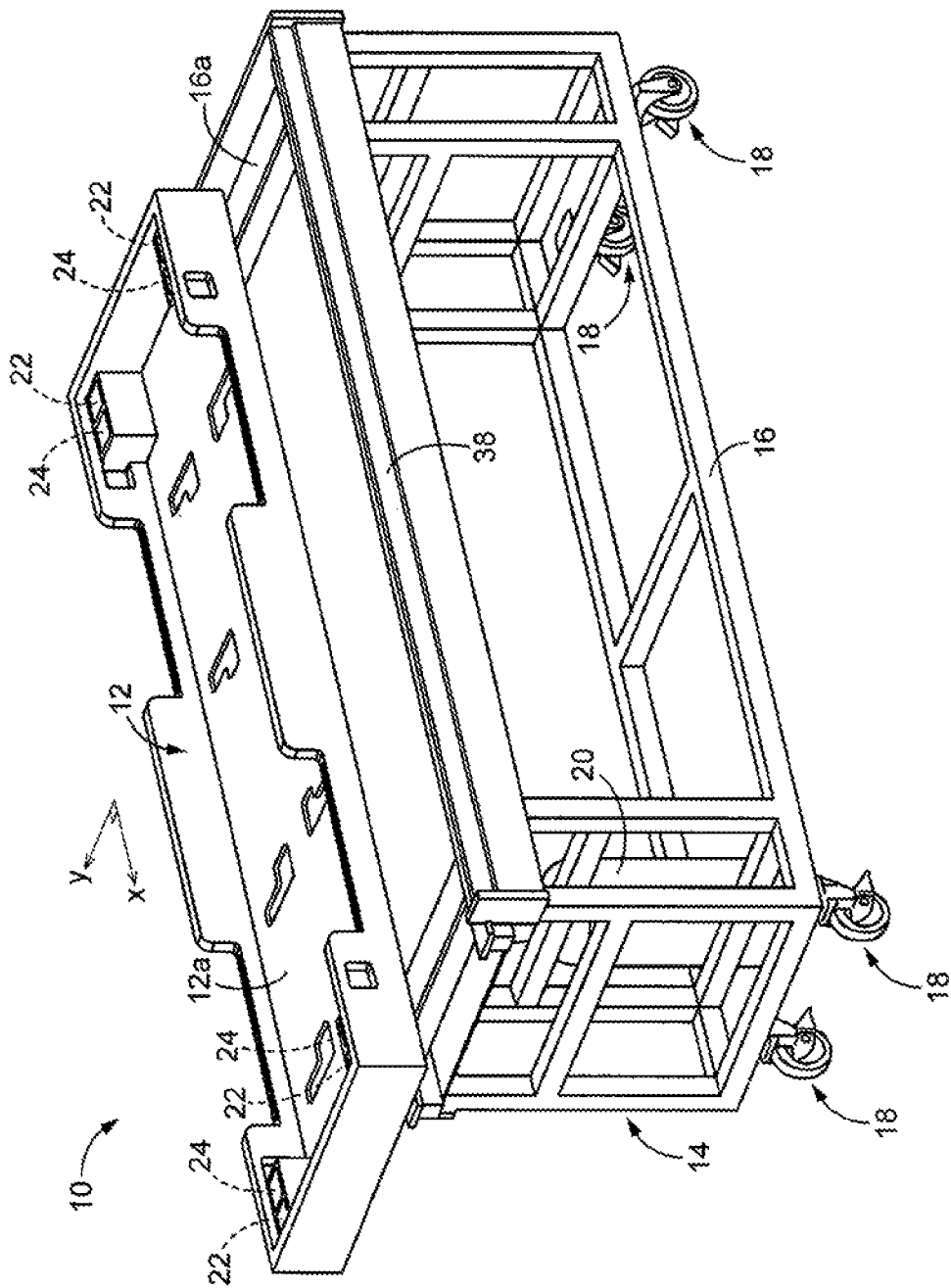
FIG. 5 is a perspective view of how the subject placement portion is moved in the short side direction relative to the carrying device in the stretcher of FIG. 1.

In the pneumatic circuit 40, when the first valve 44 is put into the second state of the valve to allow communication between the coupling portion 42 and the plurality of the cylinders 34, the gas pressure of the gas cylinder 20 is supplied to the plurality of the cylinders 34. In this state, the pistons 36 are pushed out relative to the cylinders 34 by the gas pressure supplied from the gas cylinder 20, and the wheels 32 are at least partially protruded from the bottom surface 12b in the set of the wheel units 24. On the other hand, if the first valve 44 is put into the second state of the valve, the gas pressure of the gas cylinder 20 is not supplied to the plurality of the cylinders 28. Therefore, the wheels 26 are not protruded from the bottom surface 12b in the set of the wheel units 22 and are kept in the state of being stored in the subject placement portion 12. In particular, a set of the wheels 32 in the set of the wheel units 24 disposed correspondingly to the movement in the short side direction of the subject placement portion 12 is brought into contact with the mounting table 16a, and the subject placement portion 12 is put into a state of being separated (lifted) from the mounting table 16a by the plurality of the cylinders 34. In this state, because of the rotation of each wheel included in the set of the wheels 32 in the set of the wheel units 24, as shown in FIG. 5, the subject placement portion 12 is easily moved (transferred) in the short side direction (the y-axis direction shown in FIG. 5) relative to the carrying device 14 (the mounting table 16a). FIG. 5 exemplarily illustrates a form in which the subject placement portion 12 is moved while the side plate 38 in the direction of the movement of the subject placement portion 12 is removed, out of the pair of the side plates 38 attached to the frame 16.

In the case of switching from the state of protruding the wheels 26 in the set of the wheel units 22 and storing the wheels 32 in the set of the wheel units 24, or the state of storing the wheels 26 in the set of the wheel units 22 and protruding the wheels 32 in the set of the wheel units 24, to the state of storing both the wheels 26, 32 in the sets of the wheel units 22, 24, first, the first valve 44 is put into the fourth state of the valve to interrupt the communication between the coupling portion 42 and the plurality of the cylinders 28, 34. Subsequently, the plurality of the cylinders 28, 34 and the exhaust port are allowed to communicate through the second valve 48. As a result, because of the weight (gravity force) of the subject placement portion 12 and the subject etc, placed on the subject placement portion 12, the gas is discharged (the gas pressure is relieved) from the plurality of the cylinders 28, 34, and both the wheels 26, 32 are put into the stored state. As described above, the pneumatic circuit 40 uses the gas pressure supplied from the gas cylinder 20 to selectively establish any one of the states of (a) protruding the wheels 26 in the set of the wheel units 22 and storing the wheels 32 in the set of the wheel units 24, (b) storing the wheels 26 in the set of the wheel units 22 and protruding the wheels 32 in the set of the wheel units 24, and (c) storing both the wheels 26, 32 in the sets of the wheel units 22,24.

According to this embodiment, since the stretcher 10 includes the wheels 26, 32 as the switching part switched to any one of at least two states and the cylinders 28, 34 as the switching device switching the state of the wheels 26, 32 in accordance with a supplied gas pressure, the state of the predetermined switching part in the stretcher 10 can appropriately be switched by a power source complying with a specification in which a magnetic material is not used. This enables the provision of the stretcher 10 achieving easy movement of the subject placement portion 12 from the carrying device 14.

The subject placement portion 12 includes as the switching part the set of the wheels 26 rotating in the long side direction of the subject placement portion 12 and the set of the wheels 32 rotating in the short side direction of the subject placement portion 12, and includes the cylinders 28, 34 as the switching device switching between the first state in which the wheels 26, 32 are at least partially protruded from the bottom surface 12b defined as the flat surface portion on the side opposite to the upper surface 12a defined as the flat surface portion on the side of the subject placement portion 12 on which the subject not shown is placed and the second state in which the wheels are not protruded, correspondingly to each of the set of the wheels 26 rotating in the long side direction and the set of the wheels 32 rotating in the short side direction. Therefore, the subject placement portion 12 can easily be moved relative to the carrying device 14 in both the long side direction and the short side direction of the subject placement portion 12 and, additionally, because of a comparatively simple structure, sufficient durability can be ensured even if a synthetic resin material is used for the wheel units 22, 24, for example.

Since the cylinders 28, 34 are cylinders that are driven by air pressure switching between the first state and the second state in accordance with the supplied gas pressure and the stretcher 10 includes the gas cylinder 20 mounted on the carrying device 14 and filled with the compressed gas and the pneumatic circuit 40 using the gas pressure supplied from the gas cylinder 20 to control the switching between the first state and the second state by the cylinders 28, 34, the switching by the cylinders 28, 34 can be achieved in a safe and practical form.

Since the stretcher 10 includes the subject placement portion 12, the carrying device 14, the gas cylinder 20, and the pneumatic circuit 40 (including the coupling portion 42) having major portions made of a non-magnetic material, the stretcher 10 can be provided that is preferably used at the time of examination using a nuclear magnetic resonance apparatus.

Because the stretcher 10 includes the coupling portion 42 making the gas cylinder 20 attachable to and detachable from the pneumatic circuit 40 between the subject placement portion 12 and the pneumatic circuit 40 and of including the check valve 46 preventing a backward flow of the gas from the pneumatic circuit 40 toward the coupling portion 42 on the subject placement portion 12 side relative to the coupling portion 42, the switching by the cylinders 28, 34 can be achieved by the pneumatic circuit 40 in a practical form.

Since the stretcher 10 is a device for transporting a subject fixed to the subject placement portion 12 and transferring the subject to, for example, a nuclear magnetic resonance apparatus, it is difficult to supply a gas pressure from the outside during conveyance. Since the gas cylinder 20 made of, for example, a non-magnetic material such as an aluminum alloy is mounted on the carrying device 14 and is integrally moved with the frame 16 of the carrying device 14, the stretcher 10 of this embodiment does not have to include piping, wiring, etc. disposed outside the stretcher 10, so that the pneumatic circuit 40 and thus the cylinders 28, 34 can easily be actuated at a place such as around a nuclear magnetic resonance apparatus where electric equipment cannot be used.

Another preferred embodiment of the present invention will then be described in detail with reference to the drawings. In the following description, the portions common to the embodiments are denoted by the same reference numerals and will not be described.

Second Embodiment

FIG. 6 is a perspective view for explaining an example of a configuration of a stretcher 100 that is another preferred embodiment of the present invention. The subject placement portion 12 included in this stretcher 100 includes a plurality of (in FIG. 6, four) wheel units 102 instead of the wheel units 22, 24. For example, the wheel units 102 are each disposed at one of the four corners of the subject placement portion 12. The wheel units 102 preferably have all the components made of a synthetic resin material.

Figure 10:
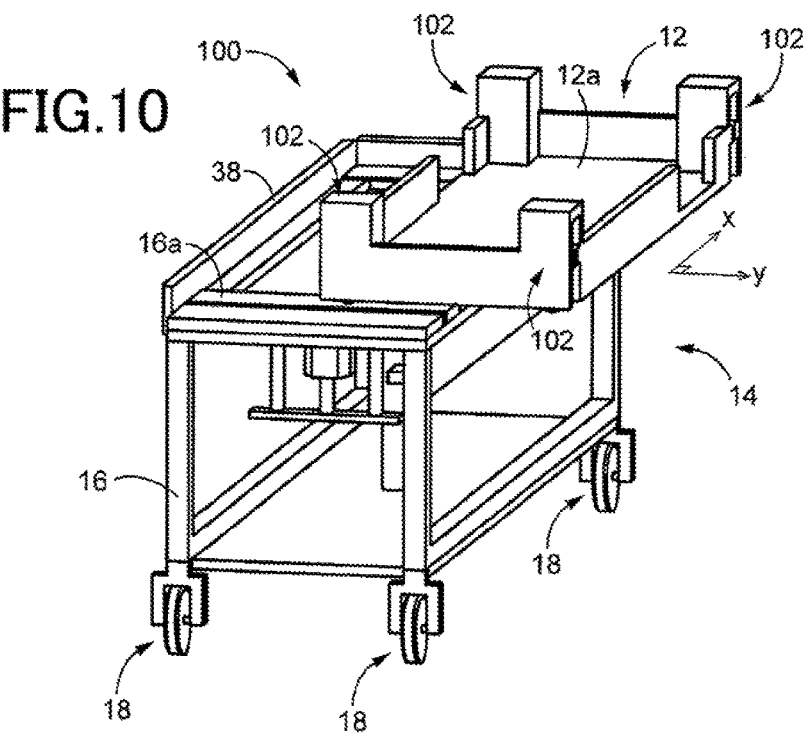
FIG. 10 is a perspective view for explaining how the subject placement portion is moved in the short side direction relative to the carrying device in the stretcher of FIG. 6, exemplarily illustrating a form of the movement with a side plate of a frame removed.
Figure 11:
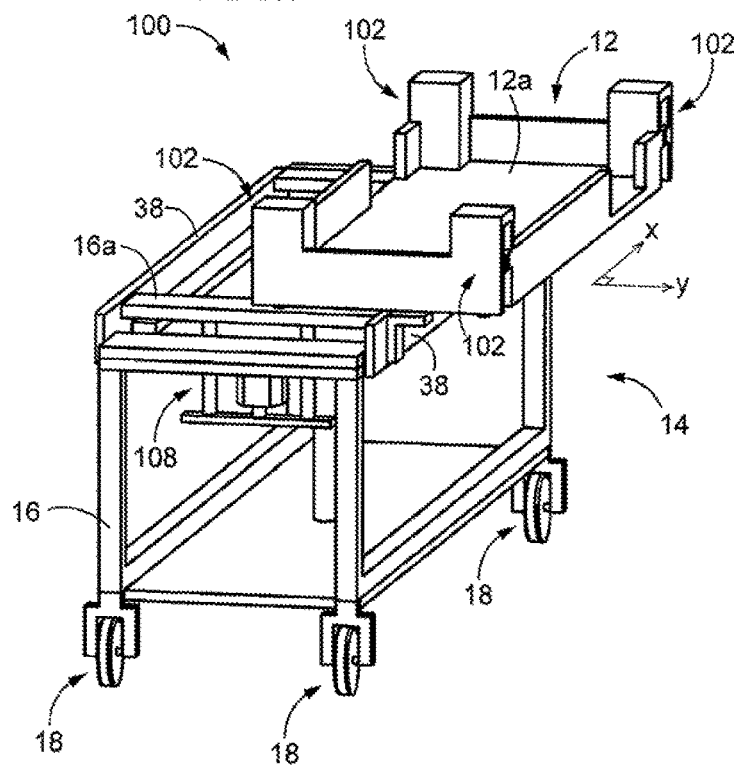
FIG. 11 is a perspective view for explaining how the subject placement portion is moved in the short side direction relative to the carrying device in the stretcher of FIG. 6, exemplarily illustrating a form of the movement of the subject placement portion elevated by an elevating device.

FIGS. 7A and 7B are schematic side views for explaining a configuration of the wheel units 102 included in the subject placement portion 12 in the stretcher 100 of this embodiment when the subject placement portion 12 is viewed in the short side direction (the y-axis direction shown in FIGS. 9 to 11). As shown in FIGS. 7A and 7B, the wheel units 102 each include a diaphragm (air spring) 106 and a wheel 104 with a direction of its axle determined such that the wheel 104 rotates in the long side direction of the subject placement portion 12. The wheel units 102 switch between a first state and a second state related to the wheels 104 in accordance with a supplied gas pressure. In particular, the diaphragms 106 are expanded by the gas pressure supplied from the pneumatic circuit 40. When a gas pressure of a predetermined value or more is supplied to the diaphragms 106 while the wheels 104 are in contact with the mounting table 16a of the frame, as shown in FIG. 7A, the wheels, 104 are at least partially protruded from the bottom surface 12b such that the subject placement portion 12 is separated from the mounting table 16a (i.e., the subject placement table 12 is lifted) against the weight (gravity force) of the subject placement portion 12 and the subject etc. placed on the subject placement portion 12. Therefore, the wheels 104 are at least partially pushed out downward from the bottom surface 12b. While the gas pressure is not supplied to the diaphragm 106 (while the gas pressure is released), as shown in FIG. 7B, the wheels 104 are pushed back by the weight of the subject placement portion 12 and the subject etc. placed on the subject placement portion 12 and are stored in the subject placement portion 12. In this embodiment, the wheels 104 correspond to the switching part switched to any one of at least two states.

In the stretcher 100 of this embodiment, preferably, the direction of rotation of the wheels 104 in the wheel units 102 can be switched by 90° (or 270°). For example, the wheels 104 can be attached and detached from the side surfaces of the subject placement portion 12 and are configured such that the wheels can be attached with the axles rotated by 90° (or 270°) in the plane parallel to the upper surface 12a of the subject placement portion 12 as shown in FIGS. 8A and 8B. After such a rearrangement, the wheel units 102 include the wheels 104 with the direction of the axles determined to rotate in the short side direction of the subject placement portion 12. Also in this form, when a gas pressure of a predetermined value or more is supplied to the diaphragms 106 while the wheels 104 are in contact with the mounting table 16a of the frame, as shown in FIG. 8A, the wheels 104 are at least partially protruded from the bottom surface 12b such that the subject placement portion 12 is separated from the mounting table 16a against the weight of the subject placement portion 12 and the subject etc. placed on the subject placement portion 12. While the gas pressure is not supplied to the diaphragm 106, as shown in FIG. 8B, the wheels 104 are pushed back by the weight of the subject placement portion 12 and the subject etc. placed on the subject placement portion 12 and are stored in the subject placement portion 12.

Therefore, in this embodiment, the wheels 104 included in the plurality of the wheel units 102 act as a set of wheels rotating in the long side direction of the subject placement portion 12 and also act as a set of wheels rotating in the short side direction of the subject placement portion 12 because of the rearrangement. In other words, the wheels 104 included in the plurality of the wheel units 102 are used as both the set of wheels rotating in the long side direction and the set of wheels rotating in the short side direction of the subject placement portion 12. The diaphragms 106 correspond to the switching device switching between the first state in which the wheels 104 are at least partially protruded from the bottom surface 12b of the subject placement portion 12 and the second state in which the wheels are not protruded, correspondingly to each of a set of the wheels 104 rotating in the long side direction and a set of the wheels 104 rotating in the short side direction, in accordance with the gas pressure supplied from the pneumatic circuit 40.

When a gas pressure of a predetermined value or more is supplied to the diaphragms 106 while the wheels 104 are attached to the plurality of the wheel units 102 so as to rotate in the long side direction of the subject placement portion 12, the wheels 104 in the set of wheel units 102 are at least partially protruded from the bottom surface 12b. In particular, the set of the wheels 104 disposed correspondingly to the movement of the subject placement portion 12 in the long side direction is brought into contact with the mounting table 16a and, as shown in FIG. 7A, the subject placement portion 12 is put into a state of being separated (lifted) from the mounting table 16a by the diaphragms 106. In this state, because of the rotation of each wheel included in the set of the wheels 104 in the set of the wheel units 102, as shown in FIG. 9, the subject placement portion 12 is easily moved (transferred) in the long side direction (the x-axis direction shown in FIG. 9) relative to the carrying device 14 (the mounting table 16a). In FIG. 9, the gas cylinder 20 is not shown (the same applies to description of FIGS. 10 and 11).

When a gas pressure of a predetermined value or more is supplied to the diaphragms 106 while the wheels 104 are attached to the plurality of the wheel units 102 so as to rotate in the short side direction of the subject placement portion 12, the wheels 104 in the set of wheel units 102 are at least partially protruded from the bottom surface 12b. In particular, the set of the wheels 104 disposed correspondingly to the movement of the subject placement portion 12 in the short side direction is brought into contact with the mounting table 16a and, as shown in FIG. 8A, the subject placement portion 12 is put into a state of being separated (lifted) from the mounting table 16a by the diaphragms 106. In this state, because of the rotation of each wheel included in the set of the wheels 104 in the set of the wheel units 102, as shown in FIG. 10 or FIG. 11, the subject placement portion 12 is easily moved (transferred) in the short side direction (the y-axis direction shown in FIGS. 10 and 11) relative to the carrying device 14 (the mounting table 16a).

As described above, a pair of the side plates 38 is attached to both side portions in the long side direction of the mounting table 16a for preventing the subject placement portion 12 placed on the mounting table 16a from falling. When the subject placement portion 12 is moved in the short side direction relative to the carrying device 14, the side plate 38 located in the movement direction of the subject placement portion 12 must be removed, or a mechanism for climbing over the side plate 38 must be included. FIG. 10 exemplarily illustrates a form in which the subject placement portion 12 is moved with the side plate 38 in the direction of the movement removed out of the pair of the side plates 38 attached to the frame 16. FIG. 11 exemplarily illustrates a form in which the subject placement portion 12 is elevated relative to the mounting table 16a by an elevating device 108 elevating and lowering the subject placement portion 12 relative to the mounting table 16a so that the subject placement portion 12 is moved in the short side direction, climbing over the side plate 38 in the direction of the movement of the subject placement portion 12. The elevating device 108 is preferably a known gas-pressure elevating device and is elevated and lowered by using a gas pressure supplied from the gas cylinder 20. The elevating device 108 is preferably made of a non-magnetic material.

According to this embodiment, the subject placement portion 12 includes the set of the wheels 104 as the switching part allowed to act as a set of wheels rotating in the long side direction and a set of wheels rotating in the short side direction of the subject placement portion 12, and the diaphragms 106 as the switching device switching between the first state in which the wheels 104 are at least partially protruded from the bottom surface 12b of the subject placement portion 12 and the second state in which the wheels are not protruded, correspondingly to each of the set of wheels rotating in the long side direction and the set of wheels rotating in the short side direction. Therefore, the subject placement portion 12 can easily be moved relative to the carrying device 14 in both the long side direction and the short side direction of the subject placement portion 12 and, additionally, because of a comparatively simple structure, sufficient durability can be ensured even if a synthetic resin material is used for the wheels 104, for example. This enables the provision of the stretcher 100 achieving easy movement of the subject placement portion 12 from the carrying device 14.

Third Embodiment

Figure 12:
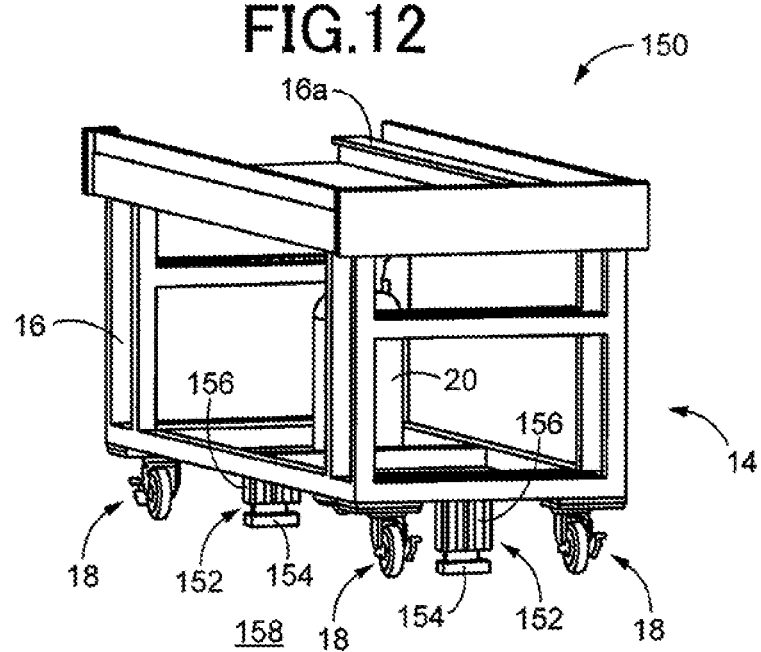
FIG. 12 is a perspective view for explaining a configuration of a stretcher that is yet another embodiment of the present invention, illustrating a state of an abutting portion abutted on a floor surface.
Figure 13:
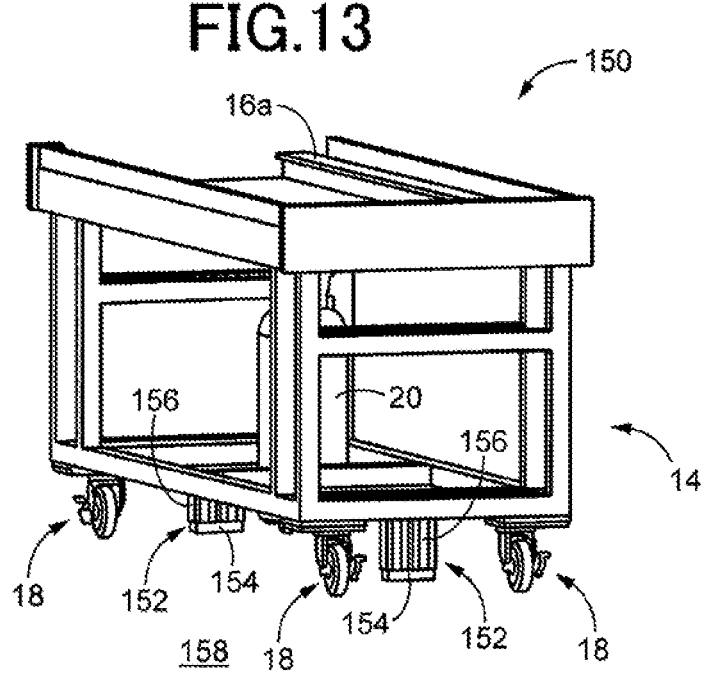
FIG. 13 is a view of a state of the abutting portion separated from the floor surface in the stretcher of FIG. 12.

FIGS. 12 and 13 are perspective views for explaining an example of a configuration of a stretcher 150 that is a further preferred embodiment of the present invention. For convenience, FIGS. 12 to 15 used in the description of this embodiment show a state in which the subject placement portion 12 is not placed on the upper portion (the mounting table 16a) of the carrying device 14. As shown in FIGS. 12 and 13, the carrying device 14 of the stretcher 150 of this embodiment includes a brake device 152. The brake device 152 includes an abutting portion 154 abutted on (pressed against) a floor surface 158 on which the carrying device 14 is located, and an actuator 156 switching in accordance with a supplied gas pressure between a first state in which the abutting portion 154 is abutted on the floor surface 158 (corresponding to FIG. 12) and a second state in which the abutting portion 154 is separated from the floor surface 158 (corresponding to FIG. 13). In other words, the actuator 156 protrudes the abutting portion 154 in the direction of the floor surface 158 in the first state and retracts the abutting portion 154 in the second state. Preferably, as shown in FIGS. 12 and 13, a plurality of (in FIGS. 12 and 13, a pair of) the brake devices 152 is included and arranged at a predetermined interval in the longitudinal direction of the mounting table 16a. The brake devices 152 preferably have all the components made of a non-magnetic material. More preferably, all the components are made of a synthetic resin material.

The stretcher 150 preferably includes a pneumatic circuit not shown using a gas pressure to control the switching between the first state and the second state by the actuator 156. More preferably, the pneumatic circuit uses a gas pressure supplied from the gas cylinder 20 to control the switching between the first state and the second state by the actuator 156.

Figure 14:
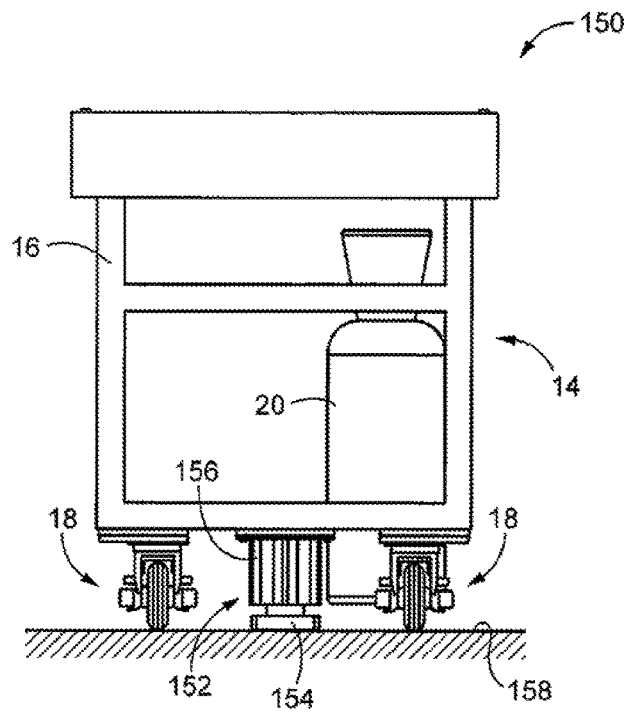
FIG. 14 is a front view illustrating the state of the abutting portion abutted on the floor surface in the stretcher of FIG. 12.
Figure 15:
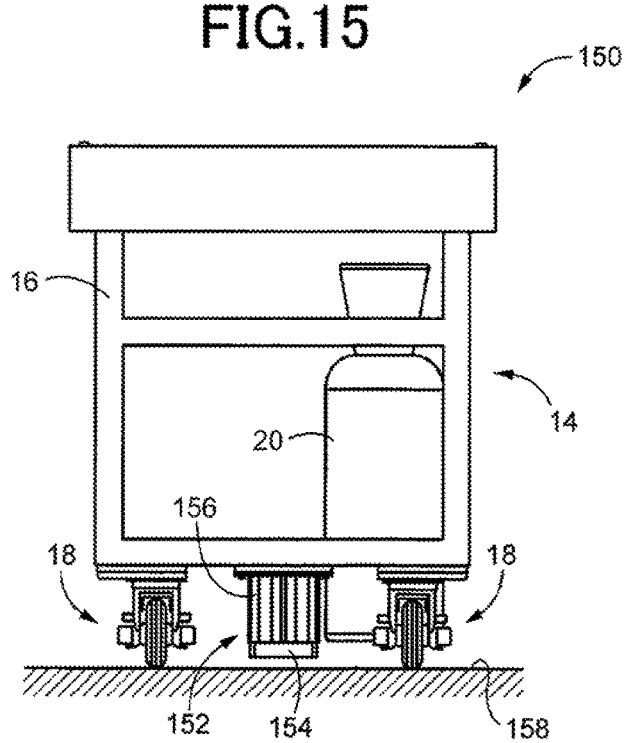
FIG. 15 is a front view illustrating the state of the abutting portion separated from the floor surface in the stretcher of FIG. 12.

FIGS. 14 and 15 are front views for explaining the actuation of the brake devices 152, and FIG. 14 corresponds to the first state in which the abutting portions 154 are abutted on the floor surface 158 while FIG. 15 corresponds to the second state in which the abutting portions 154 are separated from the floor surface 158. As shown in FIGS. 12 and 14, in the first state in which the abutting portions 154 are abutted on the floor surface 158, the carrying device 14 is restrained from moving on the floor surface 158 by a friction force between the abutting portions 154 and the floor surface 158. In particular, since a pair of the abutting portions 154 is pushed against the floor surface 158, the friction force is generated on a contact surface between the abutting portions 154 and the floor surface 158 end, consequently, the carrying device 14 is restrained from moving on the floor surface 158. In contrast, as shown in FIGS. 13 and 15, in the second state in which the abutting portions 154 are separated from the floor surface 158, the carrying device 14 is allowed to move on the floor surface 158.

According to this embodiment, the carrying device 14 includes as the switching part the brake device 152 generating a braking force by abutting the abutting portion 154 on the floor surface 158 on which the carrying device 14 is located, and includes as the switching device the actuator 156 switching in accordance with a supplied gas pressure between the first state in which the abutting portion 154 is abutted on the floor surface 158 and the second state in which the abutting portion 154 is separated from the floor surface 158 in the brake device 152 and, therefore, the braking of the carrying device 14 against the floor surface 158 can be achieved by a power source complying with a specification in which a magnetic material is not used.

Although the preferred embodiments of the present invention have been described in detail with reference to the drawings, the present invention is not limited thereto and is implemented in other forms.

For example, although an example of carrying a subject at the time of examination using a nuclear magnetic resonance apparatus is described as a form of use of the stretcher 10 in the embodiments, the present invention is not limited thereto and the stretcher may be used in various forms of use, such as carrying a subject at the time of a computed tomography (CT) inspection and carrying a subject at the time of a particle beam therapy including a proton beam therapy, for example.

Although the cylinders 28, the diaphragms 106, etc. switching in accordance with the supplied gas pressure are exemplarily illustrated as the switching device switching between the first state and the second state related to the wheels 26 etc. in the embodiments described above, the present invention is not limited to these forms. For example, the axles of the wheels 26 etc. may be made perpendicular to the mounting table 16a to achieve the second state in which the wheels 26 are not protruded from the bottom surface 12b, and a mechanism switching the axles of the wheels between the states of being parallel and perpendicular to the mounting table 16a may be included as the switching device switching between the first state and the second state related to the wheels 26 etc. The brake device 152 acting as the switching device may be applied to the stretchers 10, 100, etc. In particular, the stretcher of the present invention may include the wheels 26 etc. and the brake device 152 to switch between the first state and the second state related to the wheels 26 etc., and to switch between the first state and the second state related to the brake device 152, in accordance with a supplied gas pressure.

In the embodiments described above, the stretcher 10 includes the gas cylinder 20 mounted on the carrying device 14 and filled with a compressed gas, and the pneumatic circuit 40 using the gas pressure supplied from the gas cylinder 20 to control the switching between the first state and the second state by the cylinders 28, 34; however, the pneumatic circuit 40 may use a gas pressure supplied from outside piping etc. to control the switching between the first state and the second state by the cylinders 28, 34. It is also conceivable that the stretcher includes a vacuum pump instead of the gas cylinder 20 along with a pneumatic circuit using a suction air of the vacuum pump to control the switching between the first state and the second state by the cylinders 28, 34.

Although not exemplarily illustrated one by one, the present invention may variously be modified without departing from the spirit thereof.

REFERENCE SIGNS LIST 10, 100, 150: Stretcher 12: Subject placement portion 12a: Upper surface (Flat surface portion) 12b: Bottom surface (Flat surface portion) 14: Carrying device 26, 32: Wheels (Switching part) 28, 34: Cylinder (Switching device) 40: Pneumatic circuit 104: Wheels (Switching part) 106: Diaphragm (Switching device) 152: Brake device (Switching part) 154: Abutting portion 156: Actuator (Switching device) 158: Floor surface

The invention claimed is:

1. A stretcher having a rectangle-shaped subject placement portion on which a subject is placed and a carrying device carrying the subject placement portion, comprising:
   a switching part switched to any one of at least two states; and
   a switching device switching a state of the switching part in accordance with a supplied gas pressure, and wherein
   the at least two states include a state in which the switching part prevents movement of the subject placement portion and a state in which the switching part allows the movement, wherein
   the subject placement portion includes
   as the switching part
   a set of wheels rotating in a long side direction of the subject placement portion, and
   a set of wheels rotating in a short side direction of the subject placement portion, and wherein
   the switching device switches in accordance with the supplied gas pressure between a first state in which the set of wheels rotating in the long side direction and the set of wheels rotating in the short side direction are at least partially protruded from a flat surface portion on the side opposite to a flat surface portion on the side of the subject placement portion on which the subject is placed and a second state in which the set of wheels rotating in the long side direction and the set of wheels rotating in the short side direction are not protruded.

2. The stretcher according to claim 1, comprising a gas cylinder mounted on the carrying device and filled with a compressed gas, wherein
   the gas cylinder is made of a non-magnetic material and supplies a gas pressure to the switching device.

3. The stretcher according to claim 1, wherein
   the carrying device includes as the switching part a brake device generating a braking force by abutting an abutting portion on a floor surface on which the carrying device is located, and wherein
   the switching device switches in accordance with the supplied gas pressure between a first state in which the abutting portion is abutted on the floor surface and a second state in which the abutting portion is separated from the floor surface in the brake device.

4. The stretcher according to claim 1, wherein
   the stretcher includes a pneumatic circuit using a gas pressure to control switching between the first state and the second state by the switching device.

5. The stretcher according to claim 1, wherein
   the subject placement portion and the carrying device have major portions made of a non-magnetic material.

\* \* \* \* \*